United States Patent
Pryor et al.

(10) Patent No.: US 8,574,177 B2
(45) Date of Patent: Nov. 5, 2013

(54) PHOTOTHERAPY AND MASSAGE APPARATUS FOR TREATING MEDICAL CONDITIONS IN BODY CAVITIES

(75) Inventors: Brian Pryor, Newark, DE (US); Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 293 days.

(21) Appl. No.: 13/043,527

(22) Filed: Mar. 9, 2011

(65) Prior Publication Data

US 2011/0224584 A1  Sep. 15, 2011

Related U.S. Application Data

(60) Provisional application No. 61/312,693, filed on Mar. 11, 2010.

(51) Int. Cl.
   *A61H 1/00* (2006.01)
(52) U.S. Cl.
   USPC ............................................. 601/15; 606/14
(58) Field of Classification Search
   USPC .......... 601/15, 18, 46; 606/2, 3, 9, 13, 14, 15, 606/16, 17; 607/88, 89, 90, 92, 93, 94; 600/38

See application file for complete search history.

(56) References Cited

U.S. PATENT DOCUMENTS

| | | |
|---|---|---|
| 4,998,930 A | 3/1991 | Lundahl |
| 5,458,595 A | 10/1995 | Tadir et al. |
| 6,110,102 A * | 8/2000 | Harrison .......................... 600/38 |
| 7,144,247 B2 * | 12/2006 | Black ............................... 601/15 |
| 2001/0008973 A1* | 7/2001 | Van Zuylen et al. ............. 607/88 |
| 2006/0183072 A1* | 8/2006 | Black ............................... 601/15 |
| 2010/0179455 A1* | 7/2010 | Nebrigic et al. ................. 601/15 |

* cited by examiner

*Primary Examiner* — Quang D Thanh

(57) ABSTRACT

A phototherapy and massage apparatus is disclosed for treating medical conditions in a patient's body cavity. The phototherapy and massage apparatus comprises a light source embedded in a hollow massage wand to produce therapeutic light. The massage wand can be inserted into the patient's body cavity to provide mechanical massage to the tissue inside. A portion of the massage wand is substantially transparent to the therapeutic light such that the therapeutic light can transmit through the massage wand to provide phototherapy to the same subject tissue.

8 Claims, 1 Drawing Sheet

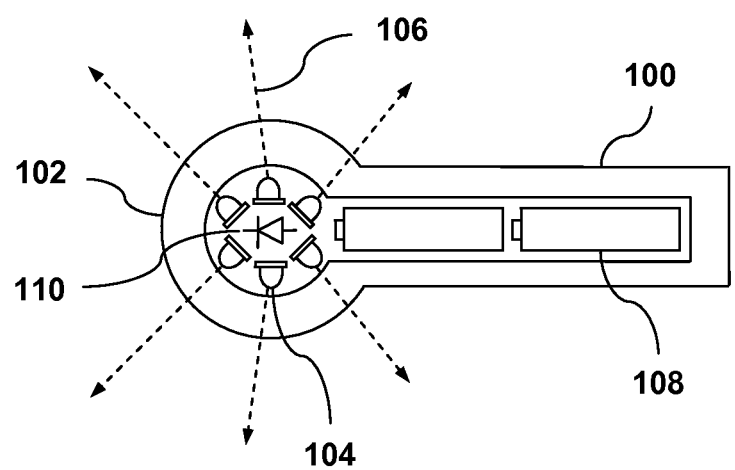

PHOTOTHERAPY AND MASSAGE APPARATUS FOR TREATING MEDICAL CONDITIONS IN BODY CAVITIES

REFERENCE TO RELATED APPLICATION

This application claims an invention which was disclosed in Provisional Patent Application No. 61/312,693, filed Mar. 11, 2010, entitled "PHOTOTHERAPY AND MASSAGE APPARATUS FOR TREATING MEDICAL CONDITIONS IN BODY CAVITIES". The benefit under 35 USC §119(e) of the above mentioned United States Provisional Applications is hereby claimed, and the aforementioned application is hereby incorporated herein by reference.

FIELD OF THE INVENTION

This invention generally relates to a phototherapy and massage apparatus, and more specifically to a phototherapy and massage apparatus for treating medical conditions in body cavities.

BACKGROUND

There are several medical conditions that cause pain in patients' body cavities. As one example, oral mucositis is an inflammatory condition of oral mucosa associated with severe pain arising from the chemotherapy agents that cancer patients must ingest as an adjunct to bone marrow transplant. As another example, there are large number of women suffer from pain in the vaginal canal, which is usually associated with an underlying medical and/or psychological condition. For instance, atrophic vaginitis (also known as vaginal atrophy), which is an inflammation of the vagina due to the thinning and shrinking of the tissues, is common for postmenopausal women as a result of decrease in estrogen level. Other examples include overactive bladder (OAB), hemorrhoids in anus, inflammation induced pain in tooth and gum, etc.

This invention discloses a new phototherapy and massage apparatus for treating medical conditions in a patient's body cavity, through which phototherapy and mechanical massage are applied to the subject tissue in a concerted manner. The two treatment methods benefit from each other thereby producing significantly improved therapeutic results.

SUMMARY OF THE INVENTION

It is the overall goal of the present invention to provide a phototherapy and massage apparatus for treating medical conditions in a patient's body cavity. The phototherapy and massage apparatus comprises a light source embedded in a hollow massage wand to produce therapeutic light. The massage wand can be inserted into the patient's body cavity to provide mechanical massage to the tissue inside. A portion of the massage wand is substantially transparent to the therapeutic light such that the therapeutic light can transmit through the massage wand to provide phototherapy to the same subject tissue. The phototherapy and massage apparatus is useful in the field of otolaryngology, gynecology, urology, gastroenterology, etc.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIG. 1 shows one exemplary embodiment of the phototherapy and massage apparatus.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a phototherapy and massage apparatus for treating medical conditions in body cavities. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

FIG. 1 shows one exemplary embodiment of the phototherapy and massage apparatus, which is used for relieving vaginal pain of a patient. The apparatus comprises a light source 104 consisting of a plurality of laser diodes, light emitting diodes (LEDs), lamps, or other types of light sources. A group of batteries 108 (or other types of power sources) are employed to provide power to the light source 104. The light source 104, as well as the batteries 108, is embedded in a hollow massage wand 100, which can be inserted into the vaginal canal of the patient. The massage wand 100 comprises a protuberance 102 made of a material substantially transparent at the output wavelength of the light source 104 such that the therapeutic light 106 can transmit through it. When a force is applied onto the massage wand 100, the protuberance 102 executes rubbing and kneading massage to the vaginal tissue. In the mean time, the therapeutic light 106 that transmits through the protuberance 102 provides phototherapy treatment to the same vaginal tissue. The plurality of laser diodes or LEDs may operate in a synchronized or unsynchronized pulse mode such that a pulsed phototherapy treatment is applied to the vaginal tissue.

Depending on the output wavelength of the light source 104, the therapeutic light 106 can provide a variety of treatment effects. The ultraviolet (UV)-blue light, at a wavelength of 370 to 490 nm, has high photon energy, which can help to produce singlet oxygen and effectively destroy bacteria. The red light, at a wavelength of 620 to 700 nm, can penetrate human tissue to a depth of about 8-10 mm. Skin layers, because of their high blood and water content, easily absorb red light, which helps to increase blood circulation and decrease inflammation/irritation. The near-infrared (NIR) light, at a wavelength of >700 nm, has been demonstrated to be beneficial for increasing cytochrome oxidase activity and ATP (adenosine triphosphate) content as well as promoting wound healing and relieving pain. In addition, the near-infrared light penetrates to a depth of about 30-40 mm, which makes it more effective for deep muscles. The light source 104 may produce therapeutic light in multiple output wavelengths, each wavelength matching with the absorption band of a specific chromophore (water, hemoglobin, lipid, protein, etc.) of the subject vaginal tissue. In addition to the above disclosed treatment effects, the therapeutic light 106 may be used to activate photosensitizing drugs for photodynamic therapy (PDT).

In this exemplary embodiment, the mechanical massage and phototherapy work in a concerted manner. The mechanical massage causes an increase in blood circulation and fluid mobilization of the subcutaneous tissue, which helps to reduce tissue inflammation and relieve muscle pain. At the same time, the massage action also causes a reduction in tissue thickness and an increase in tissue density. This change in tissue property helps to reduce the overall absorption and scattering loss of therapeutic light in the tissue and allows the therapeutic light 106 to penetrate deeper into the tissue and induce stronger photochemical reactions. The photochemical reaction in turn help to enhance the effect of the mechanical massage by stimulating inter or intra cellular response, increasing micro-circulation, etc.

In a slight variation of the present embodiment, the massage wand 100 and the protuberance 102 may have an optically diffusive outer surface, which is capable of increasing the spread angle of the transmitted therapeutic light 106. When the massage wand 100 and the protuberance 102 are not in contact with the vaginal tissue, the increased spread angle of therapeutic light helps to reduce its light intensity thus enhances the safety level of the phototherapy apparatus. When the massage wand 100 and the protuberance 102 are in contact with the vaginal tissue, the therapeutic light is much less distorted or spread. This is due to the fact that the tissue in contact with the surface of the massage wand serves as an optical index matching medium, which effectively reduces diffusing or scattering of the therapeutic light. Hence, the therapeutic light is effectively delivered into the vaginal tissue with desired direction, spread angle, power density, depth, and intensity distribution.

In another variation of the present embodiment, the phototherapy and massage apparatus may further comprise a touch sensor or a pressure sensor to control the on/off status of the light source in such a way that the light source can only be turned on when the massage wand touches the vaginal tissue. This helps to improve the safety of the phototherapy apparatus by limiting inadvertent light exposure.

In yet another variation of the present embodiment, the phototherapy and massage apparatus may further comprise a temperature sensor to monitor the temperature of the vaginal tissue. The obtained temperature signal can be utilized for controlling the light energy that is delivered to the tissue. When the measured tissue temperature reaches dangerous or undesirable levels, a warning signal can be sent to the operator to shut down the light source module.

In yet another variation of the present embodiment, the phototherapy and massage apparatus may further comprise a light sensor, which only senses the ambient light or room light but not the laser light. One example of such a light sensor is a photo detector that is covered with a band-stop optical filter. The band-stop optical filter blocks the laser light yet allows the ambient light to be detected by the photo detector. This light sensor may be used as a safety mechanism in which the laser light can only be turned on inside the patient's body cavity with minimum presence of ambient or room light.

With some minor modifications to the size and shape of the massage wand, the phototherapy and massage apparatus can be used for treating medical conditions in other body cavities, such as oral, nasal, rectal, urinary, ear, and uterus cavities or other unnaturally formed body cavities.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A phototherapy and massage apparatus for treating tissue inside a patient's body cavity, said phototherapy and massage apparatus comprising:
   a hollow massage wand capable to be inserted into the patient's body cavity for providing mechanical massage to the tissue inside the body cavity;
   at least one light source embedded in said hollow massage wand for producing therapeutic light; and
   a light sensor sensitive to ambient light yet not sensitive to said therapeutic light for controlling said at least one light source to be turned on only inside the patient's body cavity;
   wherein a portion of said hollow massage wand is substantially transparent at wavelengths of said therapeutic light to transmit said therapeutic light for providing phototherapy treatment to the tissue inside the body cavity.

2. The phototherapy and massage apparatus of claim 1, wherein said therapeutic light and mechanical massage are applied to the tissue in a concerted manner, wherein said mechanical massage modifies a plurality of properties or conditions of the tissue to facilitate absorption or interaction of said therapeutic light with the tissue to improve effects of said therapeutic light, and said therapeutic light modifies a plurality of properties or conditions of the tissue to improve effects of said mechanical massage.

3. The phototherapy and massage apparatus of claim 2, wherein said mechanical massage causes a reduction in tissue thickness and an increase in tissue density to allow said therapeutic light to penetrate deeper into the tissue.

4. The phototherapy and massage apparatus of claim 1, wherein said at least one light source is selected from the group consisting of light emitting diodes (LEDs), lasers, and lamps.

5. The phototherapy and massage apparatus of claim 1, wherein said hollow massage wand comprises at least one protuberance.

6. The phototherapy and massage apparatus of claim 1, wherein said hollow massage wand has a diffusive optical surface capable of increasing a spread angle of said therapeutic light.

7. The phototherapy and massage apparatus of claim 1, further comprising batteries embedded in said hollow massage wand for providing power to said at least one light source.

8. The phototherapy and massage apparatus of claim 1, wherein said light sensor comprises a photo detector covered with a band-stop optical filter, wherein said band-stop optical filter is configured to block said therapeutic light.

* * * * *